(12) United States Patent
Kim et al.

(10) Patent No.: US 7,645,465 B2
(45) Date of Patent: Jan. 12, 2010

(54) METHOD OF PREPARING A PHARMACEUTICAL COMPOSITION COMPRISING FERMENTED GINSENG

(75) Inventors: Dong-Hyun Kim, Seoul (KR); Jong-Hoon Ryu, Seoul (KR); Eun-Ah Bae, Seoul (KR); Myung-Joo Han, Seoul (KR); Min-Kyung Choo, Seoul (KR); Eun-Kyung Park, Seoul (KR)

(73) Assignee: Kuan Industrial Co., Ltd., Seoul (KR)

( * ) Notice: Subject to any disclaimer, the term of this patent is extended or adjusted under 35 U.S.C. 154(b) by 0 days.

(21) Appl. No.: 10/511,016

(22) PCT Filed: Apr. 8, 2003

(86) PCT No.: PCT/KR03/00704

§ 371 (c)(1),
(2), (4) Date: May 31, 2005

(87) PCT Pub. No.: WO03/086440

PCT Pub. Date: Oct. 23, 2003

(65) Prior Publication Data

US 2005/0232908 A1    Oct. 20, 2005

(30) Foreign Application Priority Data

Apr. 8, 2002    (KR) ...................... 10-2002-0018844

(51) Int. Cl.
A61K 36/254    (2006.01)
A61K 36/258    (2006.01)
A21D 13/00     (2006.01)

(52) U.S. Cl. .................. 424/728; 424/93.4; 426/76

(58) Field of Classification Search ....................... None
See application file for complete search history.

(56) References Cited

U.S. PATENT DOCUMENTS

| 4,317,816 A | 3/1982 | Arichi et al. |
| 6,579,853 B2 | 6/2003 | Sakanaka et al. |

FOREIGN PATENT DOCUMENTS

| CN | 1327850 A | * | 12/2001 |
| EP | 1213026 A1 | | 6/2002 |
| JP | 60037960 A | * | 2/1985 |
| JP | 61115013 A | * | 6/1986 |
| JP | 63216432 A | * | 9/1988 |
| JP | 03277247 A | * | 12/1991 |
| JP | 07089863 A | * | 4/1995 |
| JP | 08092114 A | * | 4/1996 |
| JP | 08196269 A | * | 8/1996 |
| JP | 2001112437 A | * | 4/2001 |
| KR | 10-1997-000239 | | 1/1997 |
| KR | 10-1997-061909 | | 9/1997 |
| KR | 10-2002-0084311 | | 11/2002 |
| KR | 10-2002-0084311 A | | 11/2002 |
| WO | WO 96/40181 | | 12/1996 |
| WO | WO 00/37481 | | 6/2000 |

OTHER PUBLICATIONS

Zhang YG, Liu TP. Zhongguo Yoa Li Xue Bao. 1996: 17(1): 44-48. Abstract only.*

Bae E.-A.; Han M. J.; Choo M.-K.; Park S.-Y.; Kim D.-H. Biol. Pharm. Bull. 2002; 25(1): 58-63.*

Roberfroid MB. Am J Clin Nutr 2000; Am J Clin Nutr 71(suppl): 1682S-1687S.* http://web.archive.org/web/*/http://www.diabetic-lifestyle.com/articles/mar00_cooki_1.htm (Web Publication Date:Jun. 19, 2000). Date Accessed: Dec. 7, 2006.*

Shibata. "Chemistry and Cancer Preventing Activities of Ginseng Saponins and Some Related Triterpenoid Compounds," J. Korean Med. Sci. vol. 16 (Suppl) (2001) 28-37.*

Bae et al., Eun-Ah, "Protective Effect of Fermented Red Ginseng on a Transient Focal Ischemic Rats", Archives of Pharmacal Research, 2004, pp. 1136-1140, vol. 27, No. 11, Korea.

Park et al., Eun-Kyung, "Ginsenoside Rh2 Reduces Ischemic Brain Injury in Rats", Biol. Pharm. Bull., 2004, pp. 433-436, vol. 27, No. 3, Pharmaceutical Society of Japan, Japan.

H. Hasegawa, et al., "Main ginseng saponin metabolites formed by intestinal bacteria," Planta Med., vol. 62, No. 5, pp. 435-437 (Oct. 1996).

Costantino Iadecola, et al., "Reduced susceptibility to ischemic brain injury and N-methyl-d-aspartate-mediated neurotoxicity in cyclooxygenase-2-deficient mice," Proceedings of the National Academy of Sciences, vol. 98, No. 3, pp. 1294-1299 (Jan. 30, 2001).

Hye-Young Park, et al., "Inhibitory Effects of *Bifidobacterium* Spp . Isolated from a Healthy Korean on Harmful Enzymes of Human Intestinal Microflora," Archives of Pharmacal Research, vol. 21, No. 1, pp. 54-61 (1988).

Eun-Ah Bae, et al., "Constitutive β-Gluccosidases Hydrolyzing Ginsenoside Rb1 and Rb2 from Human Intestinal Bacteria," Biol. Pharm. Bull., vol. 23, pp. 1481-1485 (2000).

* cited by examiner

Primary Examiner—Christopher R Tate
Assistant Examiner—Amy L Clark
(74) Attorney, Agent, or Firm—Blakely, Sokoloff, Taylor & Zafman LLP

(57) ABSTRACT

A process for preparing a processed ginseng extract with enhanced pharmacological effects due to subsequent treatment is disclosed. The subsequent treatment includes an acid-treatment of ginseng and a bio-converting treatment, such as a lactic acid bacterial fermenting and an intestinal bacterial fermenting process.

3 Claims, 1 Drawing Sheet

US 7,645,465 B2

METHOD OF PREPARING A PHARMACEUTICAL COMPOSITION COMPRISING FERMENTED GINSENG

CROSS-REFERENCE TO OTHER APPLICATIONS

This Application is a National Phase of International Application No. PCT/KR03/00704, filed on Apr. 8, 2003, which claims priority from Korean Patent Application No. 10-2002-0018844, filed on Apr. 8, 2002.

BACKGROUND OF THE INVENTION

1. Technical Field

The present invention relates to novel use of processed ginseng extract and the saponin compounds isolated therefrom for preventing and treating brain stroke and brain diseases in human or mammal. More particularly, the present invention relates to novel use of processed ginseng product with enhanced pharmacological effects due to serial treatment i.e., acid-treatment and subsequent bio-converting treatment such as lactic fermenting and intestinal-bacterial fermenting process.

2. Background Art

There are two types of brain strokes: (1) ischemic stroke, which occurs from an ischemic condition of brain tissue caused by intervention or decrease of blood supply to brain, and (2) hemorrhagic stroke, which results from bleeding of brain blood vessels. About 80% of total patients suffering from brain stroke suffer the former.

It has been reported that the cause of damage of brain neuronal cells include the release of excessive excitational neuronal transmitter, the production of free radicals, the inhibition of protein synthesis, an abnormal expression of gene and the activation of immune response, etc. However, a therapeutically effective agent to protect the damage of brain neuronal cells has not yet been developed.

The inhibition of cyclooxygenase-2 (COX-2) protects activity of brain neuronal cells due to the inhibition of glutamate release caused by inhibiting the reproduction of $PGE_2$. Therefore, since many patients suffering from rheumatic disease and pains already have taken a COX-2 inhibitor, much interest has been focused on the result of their clinical investigation about the co-relation between the incidence rate of brain stroke and the population of patients having taken the drug, which may be a new target for investigating effective agents to prevent or treat brain stroke (Iadecola, C. et al., *PNAS.*, 30, pp 1294-1299, 2001).

It is known that there are many genus of *Panax* genus plants belonging to Araliaceae, for example, *Panax ginseng* distributed or cultivated in far-eastern Asia region, *Panax quinquefolia* in America and Canada, *Panax notoginseng* in China, *Panax trifolia* in eastern region of north America, *Panax japonica* in Japan, China and Nepal, *Panax pseudoginseng* in Nepal, *Panax vietnamensis* in Vietnam, *Panax elegatior, Panax wangianus* and *Panax bipinratifidus*, etc.

Hitherto, a ginseng has been widely known as a representative nutritive tonic agent.

Recently, various scientific studies on the chemical constituents and pharmacological effects of ginseng have been reported. Investigation of the unknown pharmacological effects is being studied with modern scientific approaches. Until now, it has been known that the ginseng has various pharmacological effects such as prevention of aging, anti-arteriosclerosis, treatment of hyperlipidemia, treatment of hepatic insufficiency, improvement of liver function, protection of radiation injury, immune enhancement, improvement of cerebral function, anti-thrombotic, anti-stress, anti-diabetic, anti-hypertensive, anti-tumor effects, etc.

It has been known that the main constituent of the *Panax* genus plant is dammarane-skeleton type saponin. Ginsenosides $Rb_1$, $Rb_2$, Rc, Rd, Rg1 and Re are the main saponins in *Panax ginseng*. Their biological activities are different from each other in accordance with their chemical structures.

There have been many attempts to modify the structures of the saponins to increase their pharmacological potency through processing.

Korean Patent Publication No. 10-1997-000239 issued on Jan. 21, 1997, discloses a process for preparing a processed ginseng prepared by subjecting hot temperature treatment containing high contents of ginsenoside $Rg_3$ and $Rg_5$ so as to obtain a processed ginseng having improved potency differing from the original form of ginseng.

Korean Patent Publication No. 10-1997-061909 issued on Sep. 12, 1997, discloses a process for the production of saponin metabolites such as compound K from ginseng saponins using intestinal-bacteria.

However, there have been no disclosure or suggestion about a process for preparing a processed *Panax* genus plant by serial treatment comprising acid treatment and subsequent fermentation treatment with lactic-acid bacteria or intestinal-bacteria.

The inventors of the present invention have intensively carried out the scientific investigation concerning the chemical constituents and pharmacological effects of a ginseng, in particular a processing method of a ginseng and physiological activity of the processed ginseng. As a result of the investigation, the inventors have discovered that through the serial treatment of an acid treatment and a subsequent fermentation treatment of the ginseng extract with lactic-acid bacteria or intestinal-bacteria, the extract of the processed ginseng extract shows substantially enhanced pharmacological effects. In particular, the extract prevents or treats brain strokes.

SUMMARY OF THE INVENTION

Accordingly, it is an object of the present invention to provide a use of processed ginseng extract obtained by the steps essentially comprising an acid treatment of a ginseng extract and a subsequent fermentation treatment with lactic-acid bacteria or intestinal bacteria and the saponin compounds isolated therefrom, in the manufacture of a medicament for the prevention or treatment of brain stroke disease.

And, it is another object of the present invention to provide a method of treating or preventing brain stroke disease in a mammal comprising administrating to said mammal an effective amount of the above extract and the saponin compounds isolated therefrom, together with a pharmaceutically acceptable carrier thereof.

DISCLOSURE OF THE INVENTION

In accordance with the present invention, the present invention provides a pharmaceutical composition comprising processed ginseng extract obtained by the steps essentially comprising an acid treatment of ginseng extract and a subsequent fermentation treatment with lactic-acid bacteria or intestinal-bacteria, as an active ingredient in an amount effective to treat or prevent human or mammal suffering from brain stroke and brain diseases, together with a pharmaceutically acceptable carrier.

The present invention also provides a use of ginseng extract obtained by the steps essentially comprising acid treating a ginseng extract and subsequently fermenting the extract with a lactic-acid bacteria or intestinal-bacteria in the preparation of the medicament to prevent or treat brain stroke and brain disease.

Additionally, the present invention also provides a method of treating or preventing brain stroke disease in a mammal comprising administrating to said mammal an effective amount of above described extract, together with a pharmaceutically acceptable carrier thereof.

Above described extract can be prepared by following steps.

1. 1$^{st}$ Step:

1$^{st}$ step is to subject the following acid treatment step to plant material as follows;

(1) Acid Treatment Step

Specifically, at the 1$^{st}$ step, dried plant material of *Panax* genus, for example, the root of *Panax ginseng*, is subjected to the following acid treatment; for example, about 1 to 50 times, preferably 5 to 20 times of 0.01 to 50%, preferably, 0.1 to 10% acidic component, preferably, acetic acid, citric acid, lactic acid or acid-containing food such as the fruit of *Schizandra chinensis*, is added to the plant material, and then is subjected to incubation at a temperature ranging from 20 to 80° C., preferably 40 to 70° C. for a period ranging from 1 to 48 hrs, preferably, 3 to 12 hrs. Organic solvent such as methanol, ethanol, propanol, butanol, ether and ethyl acetate, is added thereto and then is subjected to extraction to obtain organic solvent-soluble extract; the extract is neutralized with base finally to obtain the extract of chemically processed ginseng extract.

The ginseng thus processed may be dried at a lower temperature than the heating temperature of the processing procedure, i.e., a normal temperature to 80° C. by a known manner to obtain a dried processed ginseng, or it may be further processed to obtain a powdered ginseng, if necessary.

Alternatively, the processed ginseng may be extracted using a known manner to obtain a processed ginseng extract. Specifically, the processed ginseng is extracted by using a solvent, and then the solvent is removed in vacuo or in freeze-drier to obtain a processed ginseng extract as dried powders.

The solvent which may be employed herein includes water, lower alcohol such as methanol, ethanol, etc., lower ketone such as acetone, methylethylketone, etc., supercritical fluid or mixed solvent thereof.

The plant material which may be employed includes, but are not limited to, *Panax* genus plant itself such as a fresh ginseng, a white ginseng and red ginseng, a fine root of ginseng or ginseng leaves or extracts thereof, which can be used as it is, finely divided or powdered, processed product thereof and their by-product which comprises dammarane-type saponin, preferably, the root, stem, petal, leaf and fruit of *Panax ginseng, Panax quinquefiolia, Panax notoginseng, Panax trifiolia, Panax japonica, Panax pseudoginseng, Panax vietnamensis, Panax elegatior, Panax wangianus, Panax bipinratifidus* and *Panax angustifolium* and their tissue cultivates and the extract thereof, The above step (1) can be subjected to plant material prior to following 2$^{nd}$ step.

2. 2$^{nd}$ Step: Fermentation Step

The extract obtained from 1$^{st}$ step is subsequently subjected to the following bioconversion process such as fermentation with lactic acid or intestinal bacteria as follows:

For example, lactic acid bacteria or intestinal bacteria is added to the extract obtained from 1$^{st}$ step and incubated at a temperature ranging from 20 to 50° C., preferably, 25 to 40° C. for a period ranging from 8 hours to 8 days, preferably 24 hours to 3 days to obtain extract fermented with bacteria.

The incubation time varies depending on the genus of used bacteria.

The lactic acid bacteria which may be employed includes any one which can metabolize ginsenoside $Rg_3$ to ginsenoside $Rh_2$, preferably, lactic acid bacteria belonging to *Bifidobacterium* genus, more preferably, at least one or the mixture thereof selected from the group consisting of *Bifidobacterium infantis, Bifidobacterium bifidum, Lactobacillus lactis, Clostridium butyricum, Bifidobacterium* K-103, *Bifidobacterium* K-506, *Bifidobacterium* K-513, *Bifidobacterium* K-525, *Bifidobacterium* KK-1 and *Bifidobacterium* KK-2 (disclosed in *Arch. Pharm. Res.*, 21, p 54-61, 1988). The intestinal bacteria which may be employed includes any one which can metabolize ginsenoside $Rg_3$ to ginsenoside $Rh_2$, preferably, intestinal bacteria belonging to *Bacterioides, Fusobacterium* and *Eubacterium* genus, more preferably, at least one or the mixture thereof selected from the group consisting of *Bacteriodes* JY-6 (disclosed in *Biol Pharm. Bull.*, 23, pp 1481-1485, 2000), *Bacteriodes stercoris, Fusobacterium* K-60 (disclosed in *Biol. Pharm. Bull.*, bid.) and Eubacterium L-8 (disclosed in *Biol. Pharm. Bull.*, bid.).

Further to above described steps, to isolate the saponin fractions or compounds from the extract obtained from the above 2$^{nd}$ step, the following process can be adopted.

3. 3$^{rd}$ Step: Isolation Process

To isolate pharmacologically active fractions or saponin compounds from the extract prepared by 2$^{nd}$ step, water, lower alcohols such as methanol, ethanol, propanol, butanol, ethylacetate, dichloromethane, chloroform, hexane, ether, or the mixed solvent thereof can be used as an appropriate solvent to extract or isolate the fractions or compounds from the extract obtained from 2$^{nd}$ step.

Additionally, the active ingredient can be extracted or isolated by subjecting special extraction method such as supercritical fluid extraction (SFE) to obtain partially purified saponin fractions and further, silica gel column chromatographic method to isolate saponins individually thereby.

Subsequent to the above step, following processes such as a drying process by lyophilization, agitation or dilution process can be adopted in addition to the above steps, if necessary.

The following processes can be selected either or both according to the final product forms of the present invention.

4. 4$^{th}$ Step: Drying Process (1) The above ginseng extract obtained in Step 2 or 3, is concentrated in vacuo and then dried by lyophilization or spray drying.

(2) The above ginseng extract obtained in Step 2 or 3, is centrifuged to remove impurities therefrom and precipitate and the supernatant is concentrated in vacuo and then dried by lyophilization or spray drying.

Through the above 1$^{st}$ step to 2$^{nd}$ step processes, saponins such as ginsenoside $Rb_1$, $Rb_2$, Rc, etc. contained in plant material is transformed into chemically modified ginsenosides such as ginsenoside $Rg_3$ due to acid treatment or heat treatment in step 1 and then the sugar moiety at the position 3 in modified saponins is further degraded to form further modified saponins comprising degraded saponin ginsenoside $Rh_2$.

The present invention also provides a pharmaceutical composition comprising saponin compounds selected from the group consisting of ginsenoside $Rb_1$, $Rb_2$, Rc, Rd, Re, Rf, Rg1, 20-ginsenoside $Rg_3$ and the mixture thereof, preferably, 20-ginsenoside $Rg_3$ as an active ingredient in an amount effective to treat or prevent human or mammal suffering from brain diseases, together with a pharmaceutically acceptable carrier.

The present invention also provides a use of saponin compounds selected from the group consisting of ginsenoside $Rb_1$, $Rb_2$, Rc, Rd, Re, Rf, Rg1, 20-ginsenoside $Rg_3$ and the mixture thereof, preferably, 20-ginsenoside $Rg_3$ in the preparation of the medicament to prevent or treat brain stroke and brain diseases.

Additionally, the present invention also provides a method for treating or preventing brain stroke and brain diseases in a mammal comprising administrating to said mammal an effective amount of saponin compounds selected from the group consisting of ginsenoside $Rb_1$, $Rb_2$, Rc, Rd, Re, Rf, Rg1, 20-ginsenoside $Rg_3$ and the mixture thereof, preferably, 20-ginsenoside $Rg_3$, together with a pharmaceutically acceptable carrier thereof.

The inventive composition may additionally comprise conventional carriers, adjuvants or diluents in accordance with a using method. It is preferable that said carrier is used as an appropriate substance according to the usage and application method, but it is not limited. Appropriate diluents are listed in the written text of Remington's Pharmaceutical Science (Mack Publishing co, Easton Pa.).

Hereinafter, the following formulation methods and excipients are merely exemplary and in no way limit the invention.

The composition according to the present invention can be provided as a pharmaceutical composition containing pharmaceutically acceptable carriers, adjuvants or diluents, e.g., lactose, dextrose, sucrose, sorbitol, mannitol, xylitol, erythritol, maltitol, starches, acacia rubber, alginate, gelatin, calcium phosphate, calcium silicate, cellulose, methyl cellulose, polyvinyl pyrrolidone, water, methylhydroxy benzoate, propylhydroxy benzoate, talc, magnesium stearate and mineral oil. The formulations may additionally include fillers, anti-agglutinating agents, lubricating agents, wetting agents, flavoring agents, emulsifiers, preservatives and the like. The compositions of the present invention may be formulated so as to provide quick, sustained or delayed release of the active ingredient after their administration to a patient by employing any of the procedures well known in the art.

For example, the compositions of the present invention can be dissolved in oils, propylene glycol or other solvents that are commonly used to produce an injection.

Suitable examples of the carriers include physiological saline, polyethylene glycol, ethanol, vegetable oils, isopropyl myristate, etc., but are not limited to them. For topical administration, the compounds of the present invention can be formulated in the form of ointments and creams.

Pharmaceutical formulations containing the present composition may be prepared in any form, such as oral dosage form (powder, tablet, capsule, soft capsule, aqueous medicine, syrup, elixirs pill, powder, sachet, granule), or topical preparation (cream, ointment, lotion, gel, balm, patch, paste, spray solution, aerosol and the like), or injectable preparation (solution, suspension, emulsion).

The composition of the present invention in pharmaceutical dosage forms may be used in the form of their pharmaceutically acceptable salts, and also may be used alone or in appropriate association, as well as in combination with other pharmaceutically active compounds.

The desirable dose of the inventive extract or compounds varies depending on the condition and the weight of the subject, severity, drug form, route and period of administration, and may be chosen by those skilled in the art.

However, in order to obtain desirable effects, it is generally recommended to administer at the amount ranging 0.1-10 g/kg, preferably, 1 to 5 g/kg by weight/day of the inventive extract or compounds of the present invention. The dose may be administered in single or divided into several times per day. In terms of composition, the complex herbal composition should be present between 0.01 to 80% by weight, preferably 0.5 to 50% by weight based on the total weight of the composition.

The pharmaceutical composition of the present invention can be administered to a subject animal such as mammals (rat, mouse, domestic animals or human) via various routes. All modes of administration are contemplated, for example, administration can be made orally, rectally or by intravenous, intramuscular, subcutaneous, intracutaneous, intrathecal, epidural or intracerebroventricular injection.

The present inventors demonstrated that the present composition comprising the above described ginseng extract or compounds of the present invention can be used to prevent or treat brain stroke.

Accordingly, it is another object of the present invention to provide a health care food comprising above described extract or compounds of the present invention prepared by the above processes and a sitologically acceptable additive to prevent brain stroke and brain diseases.

Above described composition therein can be added to food, additive or beverage for prevention of brain stroke diseases. For the purpose of preventing brain stroke diseases, wherein, the amount of above described extract or compounds of the present invention in food or beverage may generally range from about 0.1 to 15 w/w %, preferably 1 to 10 w/w % of total weight of food for the health food composition and 1 to 30 g, preferably 3 to 10 g on the ratio of 100 ml of the health beverage composition.

Providing that the health beverage composition of the present invention contains the above described extract or compounds of the present invention as an essential component in the indicated ratio, there is no particular limitation on the other liquid component, wherein the other component can be various deodorant or natural carbohydrates and the like such as a conventional beverage. Examples of aforementioned natural carbohydrates are monosaccharide such as glucose, fructose etc; disaccharide such as maltose, sucrose, etc.; conventional sugar such as dextrin, cyclodextrin; and sugar alcohol such as xylitol, and erythritol, etc. As other deodorants than aforementioned ones, natural deodorants such as taumatin, steviau extract such as levaudioside A, glycyrrhizin et al., and synthetic deodorants such as saccharin, aspartam et al., may be useful favorably. The amount of above described natural carbohydrate generally ranges from about 1 to 20 g, preferably 5 to 12 g in the ratio of 100 ml of the present beverage composition.

Other components than the aforementioned composition include various nutrients, vitamins, minerals or electrolytes, a synthetic flavoring agent, a coloring agent and improving agent in case of cheese chocolate et al., pectic acid and the salt thereof, alginic acid and the salt thereof, organic acid, protective colloidal adhesive, a pH controlling agent, a stabilizer, a preservative, glycerin, alcohol, a carbonizing agent used in carbonate beverage et al. Other components than the aforementioned ones may be fruit juice for preparing natural fruit juice, a fruit juice beverage and a vegetable beverage, wherein said component can be used independently or in combination. The ratio of the components is not so important but generally ranges from about 0 to 20 w/w % per 100 w/w % present composition.

Examples of addable food comprising the aforementioned extract therein or compounds of the present invention are various foods, beverages, gums, vitamin complexes, health improving foods and the like.

It will be apparent to those skilled in the art that various modifications and variations can be made in the compositions, use and preparations of the present invention without departing from the spirit or scope of the invention.

BRIEF DESCRIPTION OF THE DRAWINGS

The above and other objects, features and other advantages of the present invention will be more clearly understood from the following detailed description taken in conjunction with the accompanying drawing, in which.

BEST MODE FOR CARRYING OUT THE INVENTION

Figure 1:
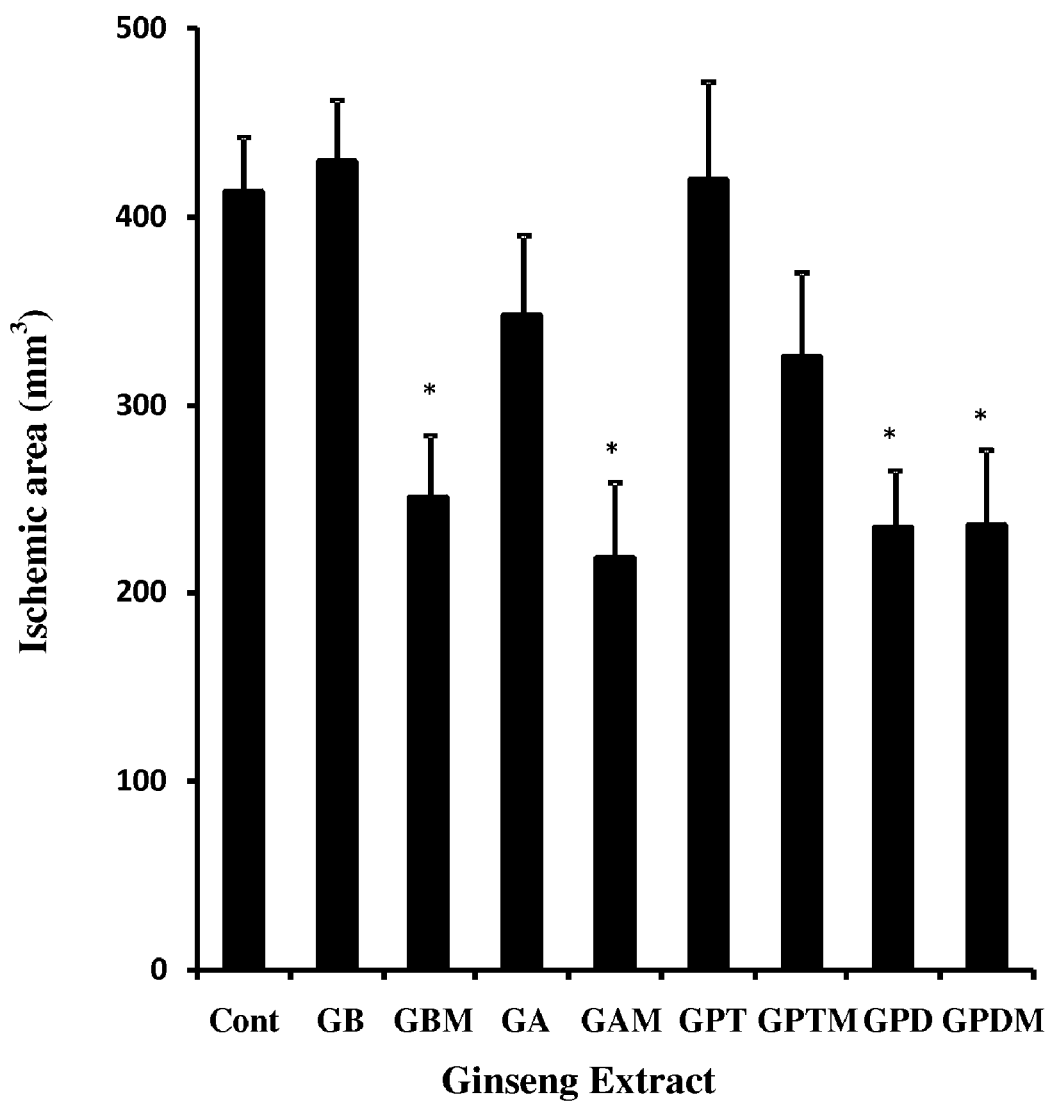
FIG. 1 shows the effect of a processed ginseng extract and saponin compounds thereinfrom.

The present invention is more specifically explained by the following examples. However, it should be understood that the present invention is not limited to these examples in any manner.

Example 1

Preparation of Processed Ginseng Extract (1)

500 g of six-year *Panax ginseng* root procured from Kyung Dong Market, was sliced into pieces, extracted with 5 L of methanol at five times and concentrated to obtain 25 g of non-processed ginseng extract. The extract was dissolved in 30 ml of distilled water, extracted with 1500 ml of butanol at four times and concentrated to obtain 10 g of butanol fraction. Each 10 g of *Bifidobacterium* KK-1 (Accession number of Depository Authority: KCCM 10364) and 10 g of *Bifildobacterium* KK-2 (Accession number of Depository Authority: KCCM 10365) were added thereto and then was incubated at 37° C. for 72 hours to obtain incubates thereof. The incubates were extracted with butanol, concentrated and dried to obtain 4 g of processed ginseng extract designated as GBM thereinafter.

Example 2

Preparation of Processed Ginseng Extract (2)

1 kg of six-year *Panax ginseng* root was sliced into pieces, extracted with 10 L of methanol at five times and concentrated to obtain 50 g of ginseng extract. The extract was dissolved in 50 ml of distilled water, extracted with 3000 ml of butanol at four times and concentrated to obtain 20 g of butanol fraction designated as GB thereinafter.

Example 3

Preparation of Processed Ginseng Extract (3)

10 g of six-year *Panax ginseng* root was sliced into pieces. 1 L of distilled water containing 0.1% lactic acid was added thereto and incubated at 60° C. for 5 hours. The pH of the cultivates was adjusted to 6.8-7.0 and extracted with 3 L of butanol at three times to obtain 6.5 g of processed ginseng extract designated as GA thereinafter.

Example 4

Preparation of Processed Ginseng Extract (4)

10 g of six-year *Panax ginseng* root was sliced into pieces. 1 L of distilled water containing 0.1% lactic acid was added thereto and incubated at 60° C. for 5 hours. The pH of the cultivates was adjusted to 6.8-7.0 and extracted with 3 L of butanol at three times to obtain 6.5 g of processed ginseng extract. Each 5 g (wet weight) of *Bifidobacterium* KK-1 (Accession number of Depository Authority: KCCM 10364, *Bifidobacterium* KK-1, deposited Mar. 29, 2002 with the Korean Culture Center of Microorganisms. 361-221, Yurim B/D, Hongje-l-dong. Seodaemun-gu, SEOUL 120-091, Republic of Korea) and *Bifidobacterium* KK-2 (Accession number of Depository Authority: KCCM 10365, *Bifidobacterium* KK-2, deposited Mar. 29, 2002 with the Korean Culture Center of Microorganisms, 361-221. Yurim B/D, Hongje-l-dong, Seodaemun-gu, SEOUL 120-091, Republic of Korea) were added thereto and then was incubated at 37° C. for 72 hours to obtain incubates thereof. The incubates were extracted with butanol, concentrated and dried to obtain 3.5 g of processed ginseng extract designated as GAM thereinafter.

Example 5

Preparation of Processed Ginseng Extract (5)

1 kg of sliced *Panax ginseng* was extracted with 10 L of methanol at five times and concentrated in vacuo to obtain 50 g of the extract. The extract was dissolved in 50 ml of distilled water, extracted with 3000 ml of butanol at four times and concentrated to obtain 20 g of butanol fraction. The fraction was further subjected to Silica gel column chromatography (Column size: 3.5×60 cm, Developing Solvent System: chloroform: MeOH=10:1) to isolate 2 g of saponin fraction containing abundant amount of ginsenoside Re, Rf and Rg1, designated as GPT thereinafter.

Example 6

Preparation of Processed Ginseng Extract (6)

1 kg of sliced *Panax ginseng* was extracted with 10 L of methanol at five times and concentrated in vacuo to obtain 50 g of the extract. The extract was dissolved in 50 ml of distilled water, extracted with 3000 ml of butanol at four times and concentrated to obtain 20 g of butanol fraction. The fraction was further subjected to Silica gel column chromatography (Column size: 3.5×60 cm, Developing Solvent System: chloroform: MeOH=10:1) to isolate 2 g of saponin fraction containing abundant amount of ginsenoside Re, Rf and Rg. Each 3 g (wet weight) of *Bifidobacterium* KK-1 (Accession number of Depository Authority: KCCM 10364) and *Bifidobacterium* KK2 (Accession number of Depository Authority: KCCM 10365) were added thereto and then was incubated at 37° C. for 72 hours to obtain incubates thereof. The incubates were extracted with butanol, concentrated and dried to obtain 1.2 g of processed ginseng extract designated as GPTM thereinafter.

Example 7

Preparation of Processed Ginseng Extract (7)

1 kg of sliced six-year *Panax ginseng* was extracted with 10 L of methanol at five times and concentrated in vacuo to obtain 50 g of the extract. The extract was dissolved in 50 ml of distilled water, extracted with 3000 ml of butanol at four times and concentrated to obtain 20 g of butanol fraction. The fraction was further subjected to Silica gel column chromatography (Column size: 3.5×60 cm, Developing Solvent System: chloroform: MeOH=10:1) to isolate 2.5 g of saponin fraction containing abundant amount of ginsenoside $Rb_1$, $Rb_2$, Rc and Rd, designated as GPD thereinafter.

Example 8

Preparation of Processed Ginseng Extract (8)

1 kg of sliced six-year *Panax ginseng* was extracted with 10 L of methanol at five times and concentrated in vacuo to obtain 50 g of the extract. The extract was dissolved in 50 ml of distilled water, extracted with 3000 ml of butanol at four times and concentrated to obtain 20 g of butanol fraction. The fraction was further subjected to Silica gel column chromatography (Column size: 3.5×60 cm, Developing Solvent System: chloroform: MeOH=10:1) to isolate 2.5 g of saponin fraction containing abundant amount of ginsenoside $Rb_1$, $Rb_2$, Rc and Rd. Each 3 g (wet weight) of *Bifidobacterium* KK-1 (Accession number of Depository Authority: KCCM 10364) and *Biflidobacterium* KK-2 (Accession number of Depository Authority: KCCM 10365) were added thereto and then was incubated at 37° C. for 72 hours to obtain incubates thereof. The incubates were extracted with butanol, concentrated and dried to obtain 2 g of processed ginseng extract designated as GPDM thereinafter.

Comparative Example 1

Preparation of Non-Processed Ginseng Extract 20 g of sliced five-year *Panax ginseng* was extracted with five times of distilled water at 60° C. for 5 hours, concentrated in vacuo with evaporator (Eyella, KN-IN model, Japan) and dried by lyophilization (Samwon Nangyul Co. SFDSM24L Model, Korea) to obtain 1 g of non-processed ginseng powder.

Comparative Example 2

Preparation of Acid Treated Ginseng Extract 20 g of five-year *Panax ginseng* root was sliced into pieces. 2000 ml of distilled water containing 0.1% lactic acid was added thereto and incubated at 60° C. for 5 hours. 5000 ml of butanol was added thereto, extracted, concentrated in vacuo with evaporator (Eyella, KN-IN model, Japan) and dried by lyophilization (Samwon Nangyul Co. SFDSM24L Model, Korea) to obtain 1.5 g of acid treated ginseng extract.

Experimental Example 1

Content Analysis Experiment

Each 2 g of extract obtained from the above Comparative Examples 1, 2 and Examples 1 and 4 were extracted with 100 ml of methanol at three times. The methanol soluble layer was concentrated in vacuo and suspended with 100 ml of distilled water. The suspension was extracted with 100 ml of ether solvent at three times, concentrated in vacuo. And further, the concentrates was extracted with 100 ml of butanol at three times and concentrated in vacuo to obtain their concentrates. The concentrates were dissolved in 100 ml of MeOH to obtain 100 mg of saponin fraction. The content analysis was subjected TLC (solvent system:chloroform:methanol:water=65: 35:10, spraying reagent:5% methanolic sulfuric acid solution) and TLC scanner (Shimadzu, CS-9301PC) as a detector. The results thus obtained are shown in Table I below.

TABLE 1

The saponin amount of Comparative Example (CE) 1, 2 and Example (E) 1, 4

| Component | The saponin amount among total saponin fraction (%) | | | |
|---|---|---|---|---|
| | CE 1 | CE 2 | E 1 | E 4 |
| Ginsenoside $Rb_1$ | 15.1 | 2.5 | <1 | <1 |
| Ginsenoside $Rb_2$ | 8.2 | 2 | <1 | <1 |
| Ginsenoside Rc | 9.5 | 1.8 | <1 | <1 |
| Ginsenoside Rd | 3.5 | <1 | 4.5 | <1 |
| Ginsenoside $Rg_3$ | <1 | 25 | <1 | 9 |
| Ginsenoside F2 | <1 | <1 | 5.5 | 0.9 |
| Compound K | <1 | <1 | 16.1 | 1.5 |
| Ginsenoside $Rh_2$ | <1 | <1 | <1 | 14 |
| Protopanaxadiol | <1 | <1 | <1 | 1.5 |

As a result, while the content of ginsenoside F2 and compound K was significantly increased in Example 1 treated with lactic acid bacteria, the content of ginsenoside $Rg_3$, $Rh_2$ and protopanaxadiol was significantly increased in Example 4 treated with acid and subsequent lactic acid bacteria.

Experimental Example 2

Preventing or Treating Activity for Brain Stroke

In order to confirm the preventing or treating activity of processed ginseng extract and saponin compounds isolated therefrom for brain stroke and to compare the activity of the inventive extract and saponin compounds with those of non-processed ginseng extract in Comparative Example 1 and acid-treated ginseng extract in Comparative Example 2, the experiment was performed by the following procedure.

Method

At about five minutes before reperfusion, various concentrations of test samples were administrated to an ischemic brain animal model. And then, re-perfusion was started. At 24 hours after the $1^{st}$ operation, the animal was killed to analyze its brain which was further cut into brain slices at the width of 2 mm using a brain matrix and stained with 2,3,5-triphenyltetrazolium chloride (TTC) staining method. The cerebral infarction region was analyzed with an image analysis system.

Result

As shown in FIG. 1, the processed ginseng extract of Example 1 (GBM), saponin fraction of Example 4 (GAM), saponin compounds in Example 7 (GPD) and Example 8 (GPDM) showed significant protecting activity for brain neuronal cells and it is confirmed that their activities were superior to Ebselin® (Sigma co.) and baicalein used as positive control. Control group treated with vehicle only is designated as Cont, Example 1 as GSM, Example 2 as GB, Example 3 as GA, Example 4 as GAM, Example 5 as GPT. Example 6 as GPTM. Example 7 as GPD, Example 8 as GPDM. "*" denotes that the value has significant at 95% significant level compared with the control group.

As described above, it is confirmed that processed ginseng extract prepared by the present invention shows therapeutic and protective effect for brain stroke and thus, it is useful for anti-brain stroke drug or health care food.

Experimental Example 3

Toxicity Test

Methods (1)

The acute toxicity tests on ICR mice (mean body weight 25±5 g) and Sprague-Dawley rats (235±10 g, Hyochang Science) were performed using the extract of the Example 1. Four groups consisting of 10 mice or rats were administrated orally with 500 mg/kg, 725 mg/kg, 1000 mg/kg and 5000 mg/kg of test sample or solvents (0.2 ml, i.p.), respectively, and observed for 2 weeks.

Methods (2)

The acute toxicity tests on ICR mice and Sprague-Dawley rats were performed using the extract of the Example 1. Four groups consisting of 10 mice or rats were administrated intraperitoneally with 25 mg/kg, 250 mg/kg, 500 mg/kg and 725 mg/kg of test sample or solvents (0.2 ml, i.p.), respectively, and observed for 24 hours.

Results

There were no treatment-related effects on mortality, clinical signs, body weight changes and gross findings in any group or either gender. These results suggested that the extract prepared in the present invention was potent and safe.

Hereinafter, the formulating methods and kinds of excipients will be described, but the present invention is not limited to them. The representative preparation examples were described as follows.

Preparation of Powder

| | |
|---|---|
| Dried powder of Example 1 | 50 mg |
| Lactose | 100 mg |
| Talc | 10 mg |

Powder preparation was prepared by mixing above components and filling sealed package.

Preparation of Tablet

| | |
|---|---|
| Dried powder of Example 1 | 50 mg |
| Corn Starch | 100 mg |
| Lactose | 100 mg |
| Magnesium Stearate | 2 mg |

Tablet preparation was prepared by mixing above components and entabletting.

Preparation of Capsule

| | |
|---|---|
| Dried powder of Example 1 | 50 mg |
| Corn starch | 100 mg |
| Lactose | 100 mg |
| Magnesium Stearate | 2 mg |

Tablet preparation was prepared by mixing above components and filling gelatin capsule by a conventional gelatin preparation method.

Preparation of Injection

| | |
|---|---|
| Dried powder of Example 1 | 50 mg |
| Distilled water for injection | optimum amount |
| PH controller | optimum amount |

Injection preparation was prepared by dissolving active component, controlling pH to about 7.5 and then filling all the components in 20 ml ample and sterilizing by a conventional injection preparation method.

Preparation of Liquid

| | |
|---|---|
| Dried powder of Example 1 | 0.1~80 g |
| Sugar | 5~10 g |
| Citric acid | 0.05~0.3% |
| Caramel | 0.005~0.02% |
| Vitamin C | 0.1~1% |
| Distilled water | 79~94% |
| $CO_2$ gas | 0.5~0.82% |

Liquid preparation was prepared by dissolving active component, filling all the components and sterilizing by a conventional liquid preparation method.

Preparation of Health Care Food

| | |
|---|---|
| Extract of Example 1 | 1000 mg |
| Vitamin mixture | optimum amount |
| Vitamin A acetate | 70 μg |
| Vitamin E | 1.0 mg |
| Vitamin $B_1$ | 0.13 mg |
| Vitamin $B_2$ | 0.15 mg |
| Vitamin B6 | 0.5 mg |
| Vitamin B12 | 0.2 μg |
| Vitamin C | 10 mg |
| Biotin | 10 μg |
| Amide nicotinic acid | 1.7 mg |
| Folic acid | 50 μg |
| Calcium pantothenic acid | 0.5 mg |
| Mineral mixture | optimum amount |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |
| Calcium carbonate | 100 mg |
| Magnesium chloride | 24.8 mg |

The above-mentioned vitamin and mineral mixture may be varied in many ways. Such variations are not to be regarded as a departure from the spirit and scope of the present invention.

Preparation of Health Beverage

| Extract of Example 1 | 1000 mg |
|---|---|
| Citric acid | 1000 mg |
| Oligosaccharide | 100 g |
| Apricot concentration | 2 g |
| Taurine | 1 g |
| Distilled water | 900 ml |

Health beverage preparation was prepared by dissolving active component, mixing, stirring at 85° C. for 1 hour, filtering and then filling all the components in 1000 ml ample and sterilizing by a conventional health beverage preparation method.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

INDUSTRIAL APPLICABILITY

The composition comprising the processed ginseng extract treated with acid and subsequent fermentation by biological treatment with lactic acid bacterial or intestinal bacterial culture according to the present invention, shows applicability to preventing or treating brain stroke. Therefore, it is useful in the prevention or treatment of brain stroke in human or mammal.

The invention claimed is:

1. A method of preparing a pharmaceutical composition for treating a stroke comprising:

treating ginseng (*Panax ginseng* or *Panax quinquefolius*) with an acid solution selected from the group consisting of acetic acid, citric acid, lactic acid, and acid from acid-containing food;

extracting the acid treated ginseng with an organic solvent to obtain an organic extract;

subsequently fermenting the organic extract with lactic-acid bacteria *Bifidobacterium* KK-1 and *Bifidobacterium* KK-2;

subsequently isolating a pharmacologically active fraction or saponin compound from the fermented organic extract; and subsequently drying the pharmacologically active fraction or saponin compound by lyophilization or spray drying.

2. The method according to claim 1, wherein said ginseng comprises the root, stem, petal, leaf fruit and tissue cultivates thereof.

3. The method according to claim 1, wherein said pharmacologically active fraction or saponin compound is selected from the group consisting of ginsenoside Rg3, ginsenoside Rh2, and the combination thereof.

\* \* \* \* \*